United States Patent [19]
Kantner et al.

[11] Patent Number: 5,730,126
[45] Date of Patent: Mar. 24, 1998

[54] CONDUCTIVE PLASTIC STUD/EYELET WITH BASE HAVING AT LEAST ONE HOLE THEREIN

[75] Inventors: Steven S. Kantner, St. Paul; Hatim M. Carim, West St. Paul, both of Minn.

[73] Assignee: Minnesota Mining And Manufacturing Company, St. Paul, Minn.

[21] Appl. No.: 606,808

[22] Filed: Feb. 26, 1996

[51] Int. Cl.$^6$ ............................................. A61B 5/0408
[52] U.S. Cl. ............................................. 128/641; 439/909
[58] Field of Search ............................................. 128/640, 641; 607/149, 152, 153; 439/899, 909

[56] References Cited

U.S. PATENT DOCUMENTS

| | | | |
|---|---|---|---|
| 3,606,881 | 9/1971 | Woodson | 128/641 |
| 3,911,906 | 10/1975 | Reinhold, Jr. | 128/641 |
| 4,367,755 | 1/1983 | Bailey | 607/152 |
| 4,846,185 | 7/1989 | Carim | 128/641 |
| 4,938,219 | 7/1990 | Ishii et al. | 128/641 |
| 5,012,810 | 5/1991 | Strand et al. | 128/640 |
| 5,326,272 | 7/1994 | Harhen et al. | 439/86 |

FOREIGN PATENT DOCUMENTS 0 449 800   10/1991   European Pat. Off.

OTHER PUBLICATIONS

Derwent Abstract for EPO 0 449 800 (1991).

*Primary Examiner*—Lee S. Cohen
*Attorney, Agent, or Firm*—Gary L. Griswold; Walter N. Kirn; John H. Hornickel

[57] ABSTRACT

A stud/eyelet for a biomedical electrode is disclosed. The stud/eyelet has at least one hole in the base to reduce manufacturing cost, provide increased surface contact with ionically conductive media, and to increase anchorage for the ionically conductive media.

13 Claims, 3 Drawing Sheets

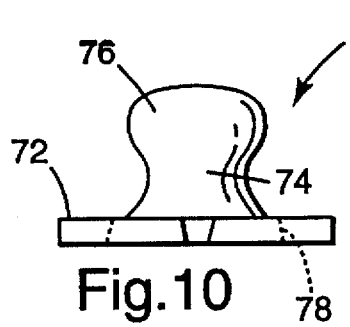
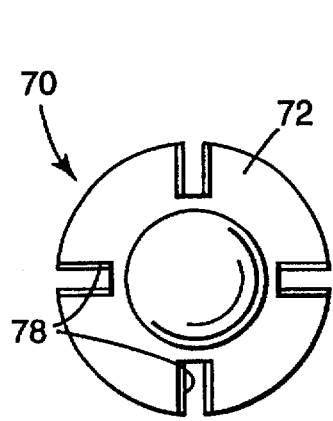
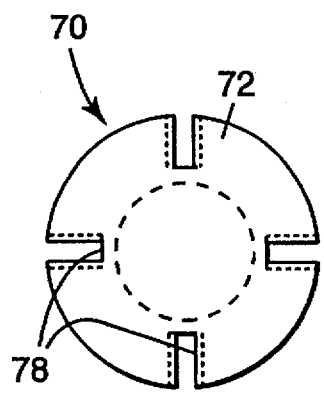
Fig.10  Fig.11  Fig.12
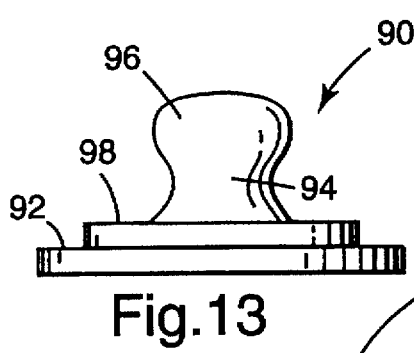
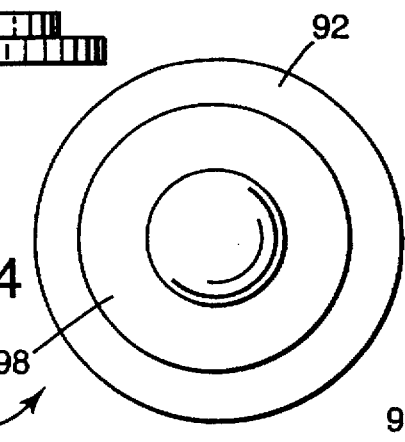
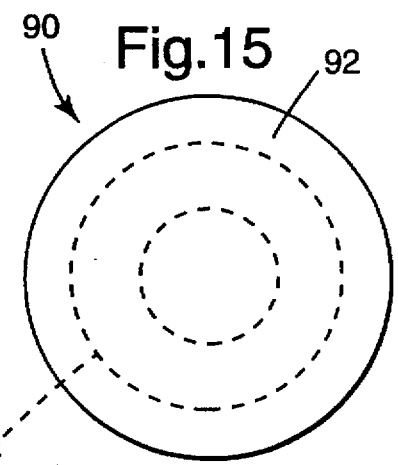
Fig.13  Fig.14  Fig.15
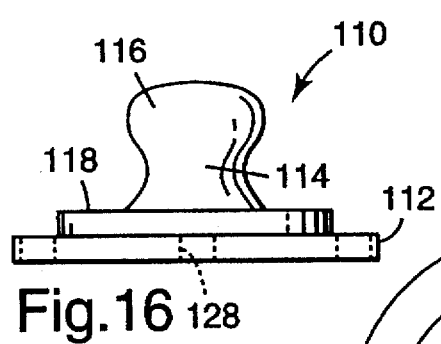
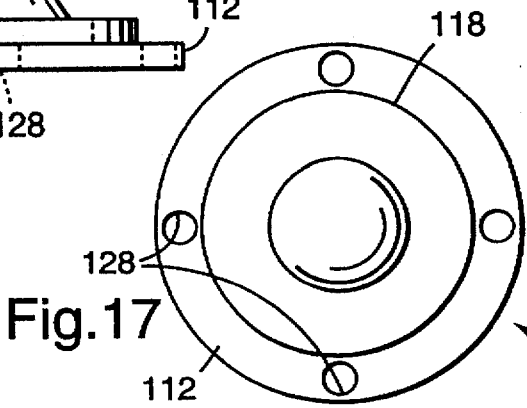
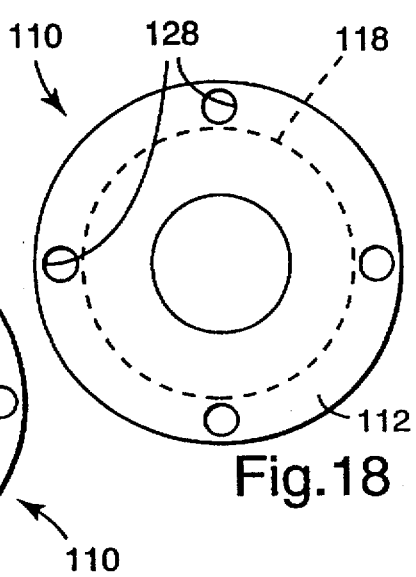
Fig.16  Fig.17  Fig.18

CONDUCTIVE PLASTIC STUD/EYELET WITH BASE HAVING AT LEAST ONE HOLE THEREIN

FIELD OF THE INVENTION

This invention relates to stud/eyelets for biomedical electrodes.

BACKGROUND OF THE INVENTION

A stud/eyelet style biomedical monitoring electrode typically comprises a backing on which is coated a pressure sensitive adhesive to adhere the electrode to the skin and an ionically conductive gel or adhesive which serves as a bridge between the skin and an electronically conductive eyelet surface which is a planar disk-like component. Attached to the eyelet and typically protruding through the backing is a post or stud which facilitates electrical connection of the electrode to the elctrocardigraph instrumentation.

The stud/eyelet components may take two different forms. The first form is a "single-piece" construction where the stud and eyelet are molded together and inserted through the electrode backing. The second form is a "two-piece" construction where the stud and eyelet are mechanically assembled top and bottom through the backing during electrode manufacture.

In certain procedures it is desirable that the stud/eyelet components be "radiolucent"—not obscuring the x-ray visualization of the tissue beneath them. In order to achieve radiolucency, the use of metal is avoided and either carbon-loaded conductive plastics or plastic articles overcoated with a thin layer of conductive metal are used.

Carbon-loaded plastics can be expensive for electrode usage, resulting in a material cost of about one cent per electrode for 0.2 grams used in certain single piece constructions. Hence minimization of material use is desirable.

A sponge or scrim is typically used to anchor the conductive gel or adhesive against the eyelet ensuring good electrical contact and preventing residue and transfer. Reliable adhesion of this sponge or scrim to the pressure sensitive adhesive of the backing may be difficult to achieve in the moist environment that the gel creates. It also adds another component to the manufacture of an electrode increasing the cost.

SUMMARY OF THE INVENTION

The present invention provides an improved stud/eyelet that improves the means for securing the ionically conductive media (e.g., gel) that also reduces cost by eliminating components (e.g., sponge or scrim).

For purposes of this invention, "stud/eyelet" can be either a two piece construction or a one piece construction.

The present invention also provides an improved quality of the interface that the ionically conductive medium (gel or adhesive) forms with the stud/eyelet. That interface is a major contributor to trace quality, because the interface of the electrode transduces ionic to electronic current.

The present invention also provides an improved electrode to recover from polarizing overloads. Polarization occurs at the conductive media/eyelet interface when an extraneous external voltage is applied to the patient wearing the electrode (e.g., a defibrillation voltage). By increasing the contact area at the interface between conductive media and stud/eyelet, an electrode with improved trace quality and an ability to more rapidly and completely recover from polarization can be obtained.

One aspect of the invention comprises placing holes in the base of the stud/eyelet to reduce material costs while improving surface contact of the stud/eyelet with ionically conductive media in the biomedical electrode.

Advantages of the stud/eyelets of the present invention are 1) anchorage for conductive adhesives or gels that are cured against the stud/eyelets, 2) increased surface area of contact between the conductive gel and the stud/eyelet resulting in improved electrical performance, and 3) reduced use of materials in fabrication resulting in lower cost.

A further advantage is found in stud/eyelets where the eyelet comprises a conductive coating or plating, such that the holes provide an electrical connection between the face of the eyelet and the back of the base on the neck side of the stud/eyelet.

Another advantage is that the placement of an adhesive, such as a hot melt adhesive through holes in the stud/eyelet allows the stud/eyelet to be more securely anchored to a backing of the electrode, particularly if the holes are frustoconically shaped.

Thus, the invention includes a stud/eyelet for a biomedical electrode, comprising a base, a neck connected to the base, and a head connected to the neck, wherein the base has at least one hole therein.

The invention also includes a biomedical electrode, comprising a nonconductive backing having an aperture; a stud/eyelet extending through the aperture wherein the stud/eyelet comprises a base, a neck connected to the base, and a head connected to the neck, wherein the base has at least one hole therein; and a field of conductive adhesive contacting the base.

Further features and advantages will become apparent from embodiments of the invention considered with reference to the following drawings.

BRIEF DESCRIPTION OF DRAWINGS

FIG. 10 illustrates a plan view of a fourth embodiment of the stud/eyelet.

FIG. 11 illustrates a top view of the embodiment of FIG. 10.

FIG. 12 illustrates a bottom view of the embodiment of FIG. 10.

FIG. 13 illustrates a plan view of a fifth embodiment of the stud/eyelet.

FIG. 14 illustrates a top view of the embodiment of FIG. 13.

FIG. 15 illustrates a bottom view of the embodiment of FIG. 13.

FIG. 16 illustrates a plan view of a sixth embodiment of the stud/eyelet.

FIG. 17 illustrates a top view of the embodiment of FIG. 16.

FIG. 18 illustrates a top view of the embodiment of FIG. 16.

EMBODIMENTS OF THE INVENTION

Figure 1:
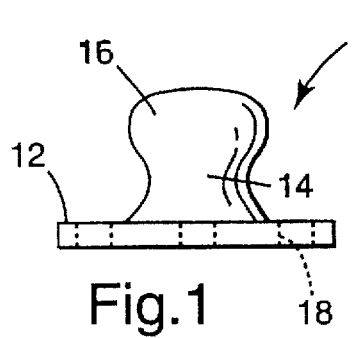
FIG. 1 illustrates a plan view of one embodiment of the stud/eyelet with holes in the base.
Figure 2:
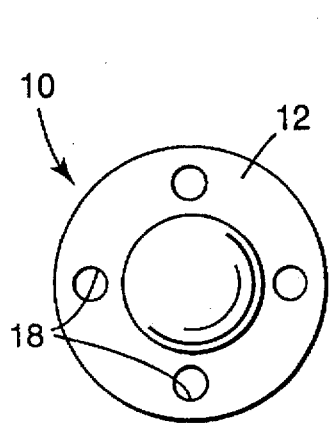
FIG. 2 illustrates a top view of the embodiment of FIG. 1.
Figure 3:
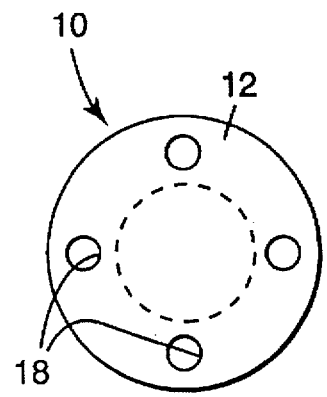
FIG. 3 illustrates a bottom view of the embodiment of FIG. 1.

FIG. 1 shows a stud/eyelet 10 having a base 12, a neck 14, and a head 16 with a plurality of holes 18 extending through the base 12. Holes 18 are orthogonal to the bottom plane of base 12 and are of substantially constant diameter. FIGS. 2 and 3 show the top view and bottom views, respectively, of this embodiment.

Figure 4:
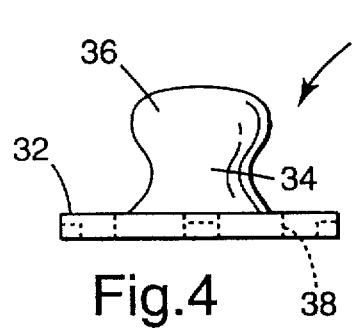
FIG. 4 illustrates a plan view of a second embodiment of the stud/eyelet.
Figure 5:
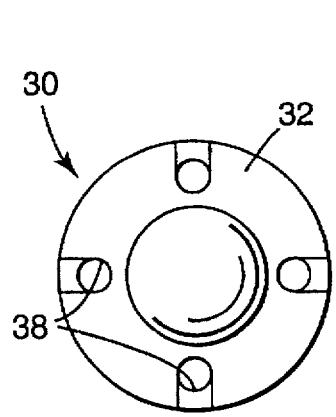
FIG. 5 illustrates a top view of the embodiment of FIG. 4.
Figure 6:
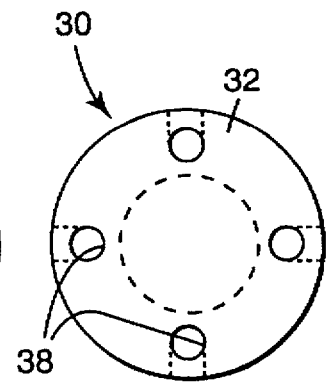
FIG. 6 illustrates a bottom view of the embodiment of FIG. 4.

FIG. 4 shows a stud/eyelet 30 having a base 32, a neck 34, and a head 36 with a plurality of holes 38 extending through the base 32. Holes 38 are orthogonal to the plane of base 32 and are of substantially constant diameter except for recesses extending on the top of the base 32 to the outer perimeter of the base 32. FIGS. 5 and 6 show the top view and bottom views, respectively, of this embodiment.

Figure 7:
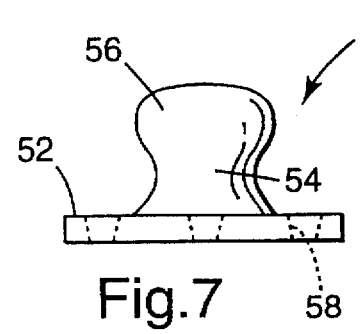
FIG. 7 illustrates a a plan view of a third embodiment of the stud/eyelet.
Figure 8:
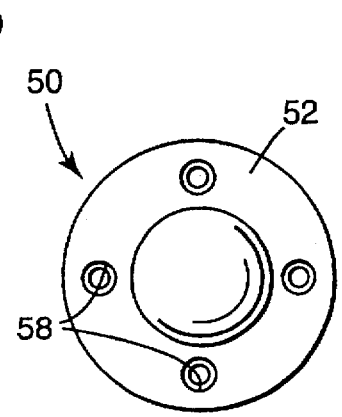
FIG. 8 illustrates a top view of the embodiment of FIG. 7.
Figure 9:
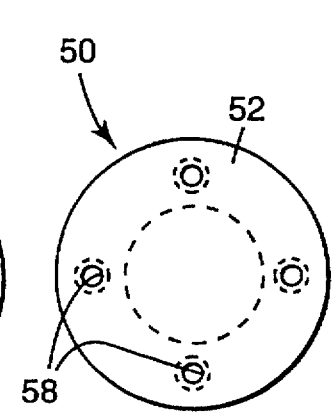
FIG. 9 illustrates a bottom view of the embodiment of FIG. 7.

FIG. 7 shows a stud/eyelet 50 having a base 52, a neck 54, and a head 56 with a plurality of holes 58 extending through the base 52. Holes 58 are orthogonal to the bottom plane of base 52 and are frustroconical in shape with the wider diameter adjacent the top plane of the base 52. FIGS. 8 and 9 show the top view and bottom views, respectively, of this embodiment.

FIG. 10 shows a stud/eyelet 70 having a base 72, a neck 74, and a head 76 with a plurality of grooves 78 (i.e., holes that contact the perimeter of the base 72) extending through the base 72 at the perimeter of base 72. Grooves 78 are orthogonal to the plane of base 72 and are frustroconical in shape with the wider diameter adjacent the top plane of the base 72. FIGS. 11 and 12 show the top view and bottom views, respectively, of this embodiment.

FIG. 13 shows a stud/eyelet 90 having a base 92, a neck 94, and a head 96 with a stepped-back rim 98 extending from the top plane of base 92 adjacent neck 94. FIGS. 14 and 15 show the top view and bottom views, respectively, of this embodiment.

FIG. 16 shows a stud/eyelet 110 having a base 112, a neck 114, and a head 116 with a stepped-back rim 118 extending from the top plane of base 112 adjacent neck 114 and also with a plurality of holes 128 extending through the base 112. Holes 128 are orthogonal to the bottom plane of base 112 and are of substantially constant diameter. This embodiment combines the embodiments of FIG. 1 and FIG. 13. FIGS. 17 and 18 show the top view and bottom views, respectively, of this embodiment.

Each of the embodiments of the present invention can be combined with any other embodiment of the present invention in order to provide the advantages of the present invention described above.

The scope of the present invention is not limited to the embodiments or their combinations described herein. The geometries of holes, grooves or rims can vary as needed. For example, holes can be curved or angular.

Each of the six embodiments described and shown in the FIGS. 1–18 provides decreased use of expensive materials, increased surface area for contact with ionically conductive media, and increased sites of anchorage of the ionically conductive media.

By allowing the ionically conductive media to penetrate into those embodiments with holes during electrode manufacture, better interfacial contact results, yielding better electrical properties. This penetration also provides anchorage of the gel against the eyelet, eliminating the need for a scrim or sponge. Penetration may be facilitated by providing channels allowing for air to escape as illustrated in FIG. 4. Certain conductive gels or adhesives may get better anchorage by being cured into holes which are wider at the top than the bottom as illustrated in FIG. 7.

Usefulness of the Invention

Stud/eyelets of the present invention can be used in biomedical electrodes for a variety of purposes.

Figure 19:
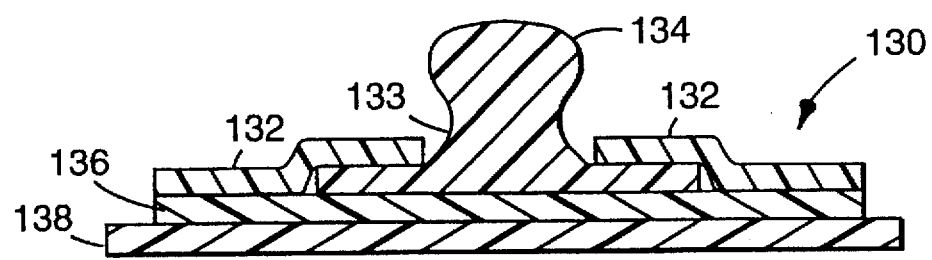
FIG. 19 is a cross-sectional view of a biomedical electrode.

A typical biomedical electrode construction is shown in FIG. 19 in cross-section. Electrode 130 has a nonconductive backing 132 having an opening 133 though which stud/eyelet 134 (in the embodiment of FIG. 1) protrudes to provide a point of electrical connection to biomedical instrumentation. Covering stud/eyelet 134 and backing 132 is a field 136 of conductive adhesive. A release liner 138 protects the field 136 prior to use.

Backing 132 can be made of any suitable insulator construction as disclosed in U.S. Pat. No. 5,012,810 (Strand et at.), the disclosure of which is incorporated by reference. Eyelet 135 can be a plastic, metallic plated eyelet (such as an ABS plastic eyelet silver-plated and chlorided and commercially available from Micron Products of Fitchburg, MA or Select Engineering of Fitchburg, Mass.).

For an additional appreciation of the scope of the invention, the claims follow.

What is claimed is:

1. A stud/eyelet for a biomedical electrode, comprising: a base having an outer perimeter, a neck connected to the base, and a head connected to the neck, wherein the base has at least one hole therein and a recess extending from at least one hole to the outer perimeter of the base.

2. The stud/eyelet of claim 1, wherein each hole is of substantially constant diameter.

3. The stud/eyelet of claim 1, wherein each hole is frustroconical.

4. The stud/eyelet of claim 1, wherein each hole is angular.

5. The stud/eyelet of claim 1, wherein each hole is curved.

6. The stud/eyelet of claim 1, wherein at least one recess contacts a perimeter of the base in a manner to form a groove.

7. A biomedical electrode, comprising:

a nonconductive backing having an aperture;

a stud/eyelet wherein the stud/eyelet comprises a base having an outer perimeter, a neck connected to the base, and a head connected to the neck and extending through the aperture, wherein the base has at least one hole therein and a recess extending from at least one hole to the outer perimeter of the base; and a field of conductive adhesive contacting the base.

8. The biomedical electrode of claim 7, wherein each hole is of substantially constant diameter.

9. The biomedical electrode of claim 7, wherein each hole is frustroconical.

10. The biomedical electrode of claim 7, wherein each hole is angular.

11. The biomedical electrode of claim 7, wherein each hole is curved.

12. The biomedical electrode of claim 7, wherein at least one recess contacts a perimeter of the base in a manner to form a groove.

13. The biomedical electrode of claim 7, wherein the stud/eyelet is secured to the backing using adhesive in at least one hole.

* * * * *